United States Patent [19]

Fontanelli

[11] Patent Number: 4,786,506

[45] Date of Patent: Nov. 22, 1988

[54] METHOD FOR THE PREPARATION OF GRANULATES SUITED FOR THE PRODUCTION OF SUSTAINED RELEASE COATED TABLETS FOR ORAL USE

[75] Inventor: Luciano Fontanelli, Pisa, Italy

[73] Assignee: Istituto Gentili S.p.A., Pisa, Italy

[21] Appl. No.: 20,450

[22] Filed: Mar. 2, 1987

[30] Foreign Application Priority Data

Mar. 11, 1986 [IT] Italy .................. 19693 A/86

[51] Int. Cl.$^4$ ................................ A61K 9/26
[52] U.S. Cl. ................... 424/470; 264/117; 264/122; 264/112; 424/478; 424/480; 424/481
[58] Field of Search ........... 264/117, 118, 122, 123, 264/112; 424/468, 469, 470, 478, 480, 481; 514/964, 965

[56] References Cited

U.S. PATENT DOCUMENTS

| | | | |
|---|---|---|---|
| 3,400,185 | 9/1968 | Kohnle et al. | 264/117 |
| 3,453,360 | 7/1969 | Hill | 264/123 X |
| 3,487,138 | 12/1969 | Hess et al. | 264/112 |
| 3,608,030 | 9/1971 | Tint | 264/113 |
| 3,629,393 | 12/1971 | Nakamoto et al. | 424/470 |
| 3,692,896 | 9/1972 | Tsumura et al. | 264/123 X |
| 3,836,618 | 9/1974 | Stevens | 264/101 |
| 3,864,469 | 2/1975 | Reiser et al. | 264/117 X |
| 3,906,086 | 9/1975 | Guy et al. | 264/117 X |
| 3,922,339 | 11/1975 | Shear | 264/118 X |
| 4,088,798 | 5/1978 | Michaelis | 514/964 X |
| 4,113,816 | 9/1978 | Estevenel et al. | 264/113 |
| 4,132,753 | 2/1979 | Blichare et al. | 264/25 |
| 4,415,547 | 11/1983 | Yu et al. | 424/469 |
| 4,591,496 | 5/1986 | Cohen et al. | 264/123 X |
| 4,684,516 | 8/1987 | Bhutani | 264/109 X |

*Primary Examiner*—Jan H. Silbaugh
*Assistant Examiner*—Mary L. Fertig
*Attorney, Agent, or Firm*—Bucknam and Archer

[57] ABSTRACT

A method for the preparation of tablets slowly releasing the active principle, characterized in that (I) during the granulation step a solution in organic solvents of a polymer insoluble in biological juices is sprayed on a mixture containing an active principle, slightly swelling polymers and usual excipients; (II) the granulated obtained in this way is added with a highly hydroswelling colloidal polymer; (III) a solution, in organic solvents, of an entero-soluble polymer, is sprayed on the granulate; (IV) the resulting granulate is submitted to compression; (V) the obtained tablets are hardened by washing with organic solvents; and (VI) they are then optionally coated.

9 Claims, No Drawings

METHOD FOR THE PREPARATION OF GRANULATES SUITED FOR THE PRODUCTION OF SUSTAINED RELEASE COATED TABLETS FOR ORAL USE

DESCRIPTION OF THE INVENTION

The present invention refers to a method for the preparation of tablets slowly releasing the active principle.

More particularly, the present invention refers to a process for the preparation of a granulate that can be transformed into tablets capable of releasing the pharmacologically active principle in a continuous way, for a period of time suited to maintain the useful concentration of the active principle in blood.

The use of long lasting drugs is at present very common. As a consequence, there is a continuous need for methods to prepare sustained release pharmaceutical compositions; these methods must be economical and must guarantee, at the same time, an effective sustained release of the active principle.

At present, the following methods are used:

(1) Micro- and macro-incapsulation:

the only difference consists in the size of the capsules, ranging from about ten micron for microcapsules to a few thousand microns for macrocapsules. There are many different preparation methods; all of them, however, are quite laborious and generally carried out by specialized centers: moreover, even though the release of their content must take place by permeability through their walls, it is to be kept in mind that other undesired mechanisms, such as breaking or dissolution of the walls, or explosion of the walls due to osmosis, are very frequent.

(2) Monolytic systems:

these methods are the easiest and cheapest, since the drug is dispersed or mixed with a polyvinyl inert matrix, and subsequently melted with it through various physical methods, including compression.

In this case, it is obvious that a remarkable amount of inert matrix must be foreseen; due to a strong dilution, some of the active substance may be dispersed after oral administration, and cannot be used before evacuation.

(3) Ion-exchanging resins system:

according to this method, the drug is directly linked to ion-exchanging resins; ionogels are also widely used; in all these cases, the release rate of the drug depends on pH and on the electrolytic concentration in the enteric tracts, and is therefore submitted to strong changes that do not make this solution the best for a sustained release.

An object of the present invention is to overcome the mentioned problems by means of a method based on the following steps:

(I) spraying a solution in organic solvents of a polymer insoluble in gastro-enteric juices, on a mixture containing the active principle, slightly hydroswelling polymers and usual excipients, in order to obtain a homogeneous-dispersion granulate;
(II) adding a highly hydroswelling colloidal polymer to the obtained granulate;
(III) spraying on the granulate a solution in organic solvents of an entero-soluble polymer;
(IV) submitting to compression the resulting granulate;
(V) hardening the tablets, by washing with the solvent used for the granulation with the entero-soluble polymer;
(VI) subjecting to optional coating the obtained tablets.

According to the desired release speed, after step (III), step (I) may be repeated.

More particularly, in step (I), the gastroresistant polymer, "a", formed by polyvinyl acetate and/or chloride or by another polymer insoluble in physiologic fluids, is sprayed in the form of a solution in organic solvents (preferably acetone) on a mixture containing the active principle, hydrophylic polymers with limited swelling ability in the presence of water, such as maize starch or animal gelatine, and excipients common in the art (magnesium stearate, etc.)

In step (II) the granulate of step (I) is enriched with absorbent colloids "c" with more marked swelling characteristics, such as gelatine, arabic gum, sodium carboxymethylcellulose (NaCMC), hydroxypropylcellulose (HPMC) and similar non ionic hydrophylic colloids.

Step (III) involves a further granulation, by means of sprinkling of a solution (in organic solvents) of a "b" entero-soluble polymer (such as shellac, cellulose acetophthalate, stearylmyristate and similar entero-soluble ethers or esters of fatty acids), in suitable dosage.

Finally, after compression, in step (IV), the obtained tablets are hardened, by means of sprinkling of the solvent used for the entero-soluble coating (generally ethyl alcohol, or ethyl acetate, according to the used raw material), on the nuclei rotating in bassine. The optional subsequent coating is carried out by means of traditional methods.

The active principle, "d", will be represented by any drug for which a long lasting action is desirable: this is the case of cardiovascular drugs, opiates, antiepileptic, antineuralgic, antiinflammatory drugs, tranquillizers, antibiotic and antidiabetic drugs, the latter, and in particular phenetyl-biguanide hydrochloride being preferred.

Obviously, for the same kind of granulation on fluid bed, the two filmings take place at random and therefore, since the same operational techniques are always used, in a completely reproducible way: in practice a part of the active principle (such as the used excipients) keeps free and available from the moment the drug is taken; on the contrary, in the part coated by the gastroresistant "b" film, the release depends on the intestine pH, and in the part coated by the "a" insoluble film, the release takes place gradually and homogeneously, but very slowly. The function of the colloids is of two main kinds: in the "a" granulate, it accelerates the release rate, whereas, when the "b" granulate with gastroresistant substance is submitted to the chemical attack connected to the different pH, the presence of highly soakable hydrophilic colloids slows it down.

The release rate of the drug is mainly bound to the relation existing between the amount of active principle (P), swelling colloids (H), insoluble polymer (I) and gastro-resistant substance (G). Common excipients (such as starch, lactose, saccharose, calcium phosphate, mannitol, glucose etc.) show little activity, provided that they are used in percentage that do not globally exceed 20% of the total weight.

It is advisable to keep the P-H-I and G ratio within the following limits: from 1:0.5:0.10:0.10 to 1:1.5:0.20:0.25.

When the ratio between I and P increases, the release rate decreases; the same thing happens when the ratio between G and P increases. On the other hand, the increase of H involves a higher release rate, and therefore, among the mentioned ratios, the more favorable ratios will be chosen in order to obtain the desired release rate.

The release is also strongly affected by the compression strength and the hardening of the table: in fact the insoluble support, under the effect of the pressure exerted during compression, forms impermeable and absolutely inert layers that create a physical barrier to the immediate contact of gelatines with biological fluids; on the other hand, the washing of nuclei in bassine, with the solvent that had been used to granulate with the gastroresistant coating (shellac, etc.) distributes it more uniformly in the tablet and on its surface, so that the immediate release of the active principle that is still free is slowed down.

The hardness of the tablets will have to be kept between 1-7 Kg/cm$^2$, because less hard tablets will immediately disintegrate as they get in contact with gastric juices, and harder tablets involve a remarkable increase in release times.

The obtained tablets, after hours in a MLI-501 Buhler rotating thermostat (30 r.p.m. rotation—temperature: 37° C.; every hour the solution is changed from pH 1.2 to pH 4.5 to pH 7.0, and finally to pH 8.0) give as a result a spongy mass, reproducing the form of the nucleus, mainly due to the insoluble polymer that creates a rigid reticular beehive-like structure.

A number of controls of "in vitro" release have been carried out on several lots of two kinds (I° and II°) of tablets, whose only differences were the quantity of the used excipients and the weight ratios of the excipients.

Both preparations contained phenethyl-biguanide hydrochloride: the analytical data of the release of the active principle during time for lots of the same kind, turned out to be completely homogeneous, confirming the productive process, and to follow the percentage values showed in Table 1, in which the weight ratios of the various excipients are also reported.

TABLE 1

| Weight ratio of Excpients | | | | % Quantity of released active principle | | | | |
|---|---|---|---|---|---|---|---|---|
| PVC/PVA (9:1) | NaCMC + gelatin | Inert Excipient | Shellac | 1 h | 2 h | 3 h | 4 h | 6 h |
| 1 | 14 | 11 | 1.9 | 25 | 52 | 70 | 100 | — |
| 1 | 7.4 | 2.7 | 0.9 | 30 | 50 | 70 | 85 | 100 |

The following preparation examples illustrate the invention.

EXAMPLE I 2000 g of active substance, 800 g of powder animal gelatine, 730 g of starch were mixed and granulated in fluid bed with 270 g of copolymer PVC-PVA (9:1) dissolved in acetone: after drying, the granulate was added to 400 g of gelatine, 800 g of NaCMC, and a new filming was carried out with 250 g of shellac dissolved in 96% alcohol.

The resulting granulate, after addition of 60 g of magnesium stearate, was compressed with 6 mm hollow punches. The tablets were then treated in rotating bassine, in subsequent turns, with the solvent used for the second filming; every time they were subsequently dried in order to be hardened.

EXAMPLE II 1000 g of active substance, 500 g of powder animal gelatine, 1450 g of starch were mixed and submitted to granulation in fluid bed by means of spraying with 130 g of copolymer PVC-PVA (9:1) dissolved in acetone: after drying, the formed granulate was added to 590 g of gelatine, 730 g of NaCMC, and a new filming with 250 g of shellac dissolved in 96% alcohol was carried out.

The obtained granulate, after addition of 55 g of Mg stearate, was submitted to compression to obtain tablets having weight 64.7 mg. The tablets were then hardened in bassine by means of several treatments with alcohol.

EXAMPLE III 2000 g of active substance, 600 g of arabic gum, 350 g of saccharose, screen sieved, 50 mesh, were mixed and sprayed in fluid bed with 400 g of polymethacrylic resin (plasticizer: triacetine 5.0 g); the granulate was directly added to 500 g of hydroxypropylmethylcellulose, 500 g of starch, 50 g of Mg stearate, and submitted to further filming with 200 g of cellulose acetophthalate dissolved in acetone: isopropanol: ethyl acetate.

After drying the granule was compressed, sieved by a 18 mesh screen, with circular hollow punches. The obtained tablets were hardened in bassine by means of subsequent additions of the solvent used in the second filming, until the desired hardness was reached.

EXAMPLE IV

The same process of Example III was followed, but animal gelatine was used instead of arabic gum, and methylcellulose instead of hydroxypropylmethylcellulose: the lower hydrophilic capacity of the two substituted excipients decreases the drug's release rate.

Tablets of the kind described above may be coated with the classic method of sugar coating: this kind of coating hardly affects the drug's release, and only during the first hour following ingestion.

What is claimed is:

1. A process for the preparation of tablets slowly releasing an active principle which consists essentially of preparing a mixture containing said active principle, a slightly swelling polymer and an excipient, then spraying onto said mixture in step (I) a solution in an organic solvent of a polymer insoluble in physiological fluids granulating said thus sprayed mixture to obtain a granulate; in step (II) adding to said granulate a hydroswelling colloidal polymer to obtain a granulate with increased swelling properties; in step (III) spraying a solution, in an organic solvent, of an entero-soluble polymer onto said granulate from step (II); in step (IV) compressing said granulate to obtain tablets; in step (V) hardening said tablets by washing with an organic solvent.

2. The process according to claim 1 wherein said tablets from step (V) are coated in step (VI).

3. The process according to claim 1, wherein after step (III), step (I) is repeated.

4. The process according to claim 1, wherein the solution sprayed in step (I) is an acetone solution of polyvinyl chloride and/or polyvinyl acetate.

5. The process according to claim 1, wherein the colloidal polymer of step (II) is a member selected from the group consisting of gelatine, arabic gum, sodium carboxymethylcellulose and hydroxypropylcellulose.

6. The process according to claim 1, wherein the entero-soluble polymer of step (III) is a member selected from the group consisting of shellac, cellulose acetophthalate and stearylmyristate.

7. The process according to claim 1, wherein said organic solvent in step (IV) is the same as the solvent used in step (III).

8. The process according to claim 1, wherein the ratio of said active principle, said polymer of step (II), said insoluble polymer of step (I), said entero-soluble polymer of step (III) is 1:0.5:0.10:0.10 to 1:1.5:0.20:0.25.

9. A pharmaceutical sustained release tablet obtained by the process of claim 1.

* * * * *